United States Patent [19]

Casper

[11] Patent Number: 4,672,437

[45] Date of Patent: Jun. 9, 1987

[54] FIBER OPTIC INSPECTION SYSTEM

[75] Inventor: Lawrence A. Casper, Plymouth, Minn.

[73] Assignee: Honeywell Inc., Minneapolis, Minn.

[21] Appl. No.: 752,435

[22] Filed: Jul. 8, 1985

[51] Int. Cl.⁴ .............................................. H04N 7/18
[52] U.S. Cl. .................................. 358/101; 350/96.18; 350/96.26; 356/241; 358/106; 358/901
[58] Field of Search ................ 358/101, 106, 107, 93, 358/901; 356/241; 350/96.18, 96.26; 382/8

[56] References Cited

U.S. PATENT DOCUMENTS

| | | |
|---|---|---|
| 3,051,166 | 8/1962 | Hovnanian . |
| 3,417,745 | 12/1968 | Sheldon . |
| 3,437,747 | 4/1969 | Sheldon . |
| 3,855,897 | 12/1974 | Takahashi et al. . |
| 4,067,937 | 1/1978 | Unno ................................ 350/96.18 |
| 4,145,714 | 3/1979 | MacDonald ........................ 356/241 |
| 4,389,669 | 6/1983 | Epstein et al. . |
| 4,423,436 | 12/1983 | Kimura . |
| 4,500,204 | 2/1985 | Ogura ................................ 350/96.26 |
| 4,581,706 | 4/1986 | Kato .................................... 358/106 |
| 4,593,406 | 6/1986 | Stone ...................................... 382/8 |

*Primary Examiner*—Howard W. Britton
*Attorney, Agent, or Firm*—William T. Udseth

[57] ABSTRACT

A fiber optic inspection system for use in the inspection of sandwiched solder bonds in integrated circuit packages. The apparatus contains a miniature fiber optic probe which picks up an image of the solder bonds and transmits it to a video camera. The video output signal of the camera is image processed to enhance the picture quality and displayed on a video monitor.

12 Claims, 3 Drawing Figures

FIBER OPTIC INSPECTION SYSTEM

The Government has rights in this invention pursuant to Contract No. DAAK20-83-C-0430 awarded by the Department of the Army ERADCOM.

BACKGROUND OF THE INVENTION

This invention relates to an image pickup device and its use in the inspection of packaged integrated circuits.

The development of high density, high speed integrated circuits has created the need for new approaches in packaging technology. Advanced package designs emphasize density of input/output lines, reduction in wiring length and reliability at the component level. Such high density designs use pin-pad arrays and other bonding approaches which sandwich the bonds between the chip carrier and the mother board. While this approach conforms to the needs of high density packaging, it creates quality control problems. Solder bonds in the final structure are hidden from view. Further, the multilayered ceramic carrier or mother board acts as a barrier to imaging or signal transmission techniques which might be applied to examine the solder bonds.

The problem of hidden bonds inspection has been in existence since the early 60's when the "Flip-Chip" package structure was successfully employed. Quality control of the flip-chip package was done by careful control of the bonding process rather than 100% visual inspection as needed to qualify the chip under Mil-Std 883B.

Until now, no known inspection technique existed to determine if solder bonds would meet the high reliability requirements for Military Standard 883B. Considering the electro-magnetic spectrum as well as particle beams there is potentially a large number of techniques capable of inspecting solder bonds. However, one important criterion must be immediately applied; the technique must not have the potential for generating failure in the device or in the associated packaging, thus eliminating penetrating radiation such as X-rays or neutrons used for radiography. Low energy radiation while not damaging the integrated circuit or the package fails to give clear results of possible defects occurring within the solder bonds. Electrical, acoustic, thermal and ultrasonic signals transmitted across the solder bond could reveal the absence of a bond. However, such techniques could not provide critical information about the size, contact angle of wetting, texture or other important information that is derived from direct visual imaging. These techniques suffer from problems of signal attenuations and modifications due to the complex composite structure of the package. These techniques also give rise to a concern about damage to the package or the device due to induced stresses.

SUMMARY OF THE INVENTION

The present invention is an apparatus and method for visually inspecting occluded areas of integrated circuit packages. A miniature fiber optic bundle is inserted into the area to be inspected. The fiber optic bundle transmits the optical image to a video camera for conversion of the optical signal to a video signal. The video signal is then transmitted to an image processing unit which can enhance the image quality before displaying the video signal on a video monitor.

DETAILED DESCRIPTION OF THE PREFERRED EMBODIMENT

Figure 1:
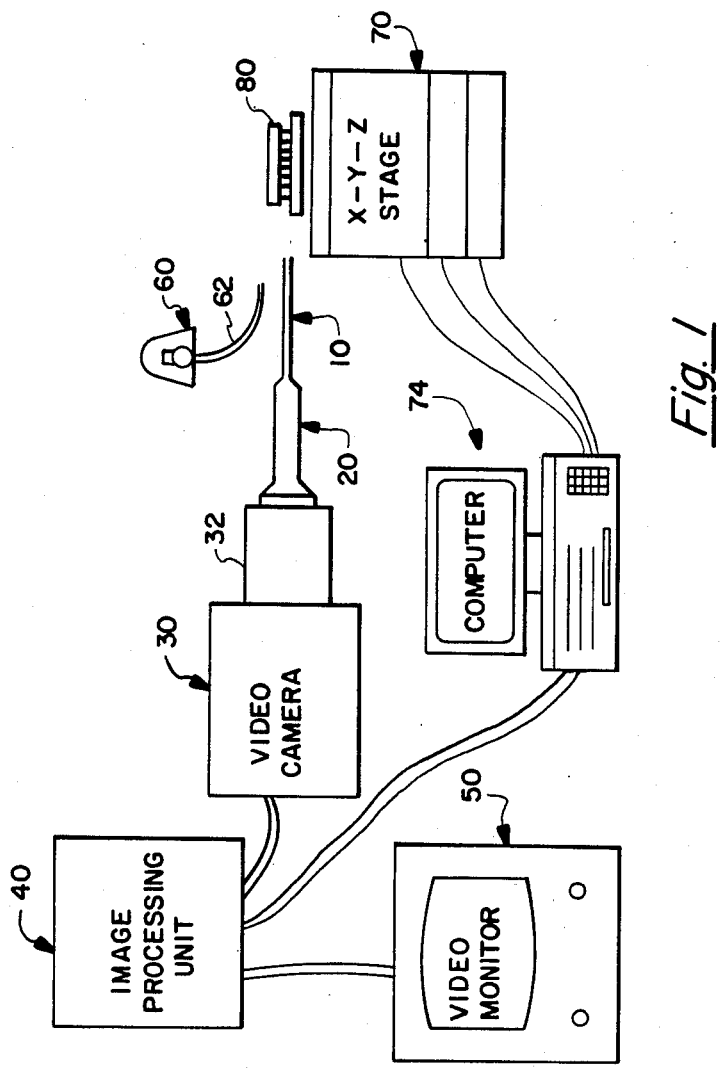
FIG. 1 shows the arrangement of the micro fiber optical system.

The fiber optic inspection system is shown in FIG. 1. The system is made up of a micro probe 10 which contains a miniature fiber optic bundle and is connected to a transfer optics tube 20. A video camera 30 with a lens 32 is coupled to the transfer optics tube 20 to pick up the optical image and convert it to a video signal. The video signal is transferred to an image processing unit 40. This system can be a Vicom (TM) or other digital image processor. The Vicom (TM) digital image processor system includes a video frame digitizer which permits up to sixteen 512×512 pixel video images to be stored in real time. It contains a resident library of image processing routines that can be utilized without modification. From the image processing unit, the video signal can be displayed on a video monitor 50. The work piece 80 to be inspected is mounted on an X-Y-Z stage 70. A computer 74 can be used to automate the inspection process by controlling the stage motion and performing pattern recognition of the viewed solder bonds.

Figure 2:
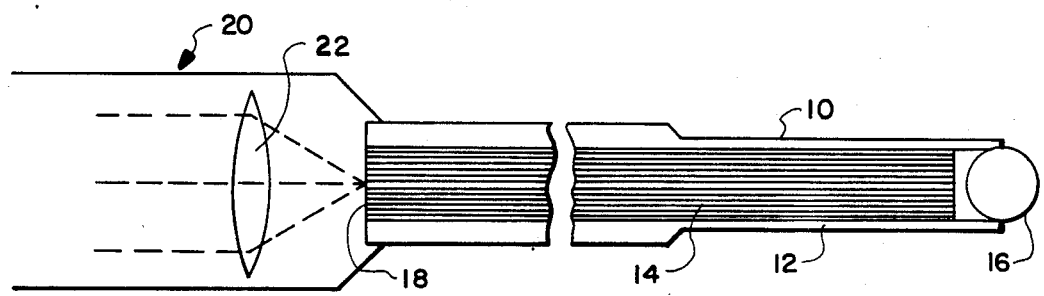
FIG. 2 is a detailed drawing of the fiber optic probe.

The fiber optic probe 10 is shown in greater detail in FIG. 2. The fiber optic probe consists of a stainless steel sheath 12 which has an outside diameter at the tip of 15 mils and an inside diameter of 10 mils. One inch from the tip the diameter is increased to 20 mils to increase stiffness. Contained within the stainless steel sheath is a fiber bundle drawn from clad optical glass rods until the fibers were about 2.5 microns in diameter. The bundle has a nominal diameter of 10 mils. The cut ends of the bundle are polished to provide a good optical surface to receive and transmit an optical image. A 10 mil diameter spherical glass or graded index fiber lens 16 is epoxied in place just inside the tip of the sheath, giving sufficient clearance for a wide field of view.

The fiber optic bundle picks up the image at the focal point of the lens and transmits the image to the viewing end of the bundle 18. The optical transfer tube 20 contains one or more lenses 22 and allows for the transmission of the optical image to the video camera 30 via the camera lens 32.

Figure 3:
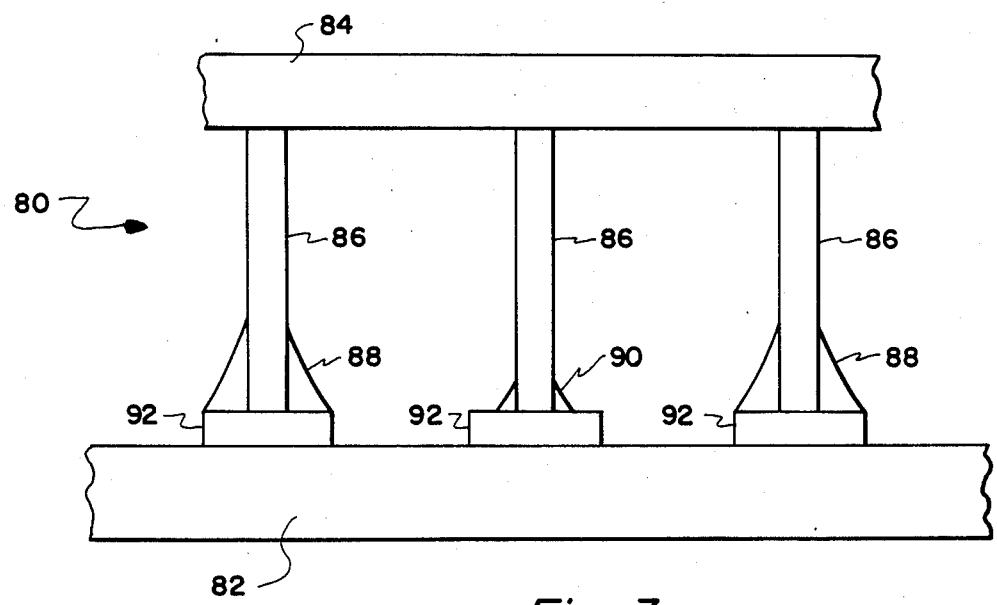
FIG. 3 shows a typical integrated circuit package for inspection.

An example of a typical integrated circuit package is shown in FIG. 3. The pin-pad array 80 contains a mother board 82 having pads 92 for electrical interconnecting with the chip carrier 84. The chip carrier contains an integrated circuit chip and an array of pins 86. In this example the pins and pads are spaced 35 mils apart with the pin having a height of 35–50 mils. The pins 86 of the chip carrier are solder bonded to the pads 92 of the mother board. Good solder bonds are shown by the numeral 88 and a defective solder bond is shown by numeral 90.

In operation, one or more video cameras 30 with attached fiber optic probes are mounted in a fixed relationship to an XYZ stage 70. On the stage is mounted the work piece 80. The height of the stage is adjusted to allow the fiber optic bundle to pass easily within the integrated circuit package to be inspected. The solder bonds which are normally spaced 35 mils apart are passed by the 15 mil diameter fiber optic probe(s) as the X-Y-Z stage transverses forward toward the probe. The stage then withdraws from the probe and advances to a new position and repeats the inspection process. The computer 74 can be used to control the motion of the X-Y-Z stage. The computer can be programmed to drive the stage with the proper spacing and array size for several different package configurations.

To provide illumination into the occluded areas of the integrated circuit package an illuminator 60 is used. To bring the illuminating light more directly to the specific area to be inspected a fiber optic bundle 62 may be used. In operation, this bundle 62 is directly attached in parallel to the fiber optic probe 10.

The experimental resolution limits of the described system were determined by use of the United States Air Force resolution test target. The system is able to resolve individual lines/pairs down to 50 microns. Without using an image processing unit 40 the human operator is able to discern the quality of a solder bond as the bond is moved past the fiber optic probe.

To ease the package inspection for the human observer and further the possibility of future automatic machine operation the image processing unit is employed. Without image processing the system is subject to variations of the illuminating light. Low light prevents adequately seeing the solder bonds and too much light causes blazing within the video camera. Image processing techniques are employed to remove the sensitivity of the fiber optic inspection system due to light level, and to automate the inspection procedure.

The enhancement include operations that were used to improve the appearance of the image to a human observer as well as the possibility of converting an image to a format better suited for automatic inspection. The Vicom (TM) digital image processor contains a resident library of image processing routines that are utilized without modification. One of these, contrast manipulation, includes a variety of operations which can be termed point operations because they transform each pixel point by point by some linear or non-linear function. The intent is to take a portion of the input image brightness which contains much of the image detail and spread the range out over a large portion of the total brightness range in the output image. This technique works fairly well using an exponential type function.

Another routine, noise cleaning, is used to eliminate random high spatial frequency clutter in the image. The individual fibers in the fiber optic image guide produce a regular pattern of noise in the image. There are several methods of noise cleaning. One is to eliminate random isolated noise pixels by comparing each pixel to the average of its nearest neighbor, and if it varies by greater than some special value, replace it by the average value. Another is to use low-pass spatial filtering since noise generally has a higher spatial frequency spectrum than normal image components. The low-pass spatial feature technique was shown to significantly reduce the noise due to the individual fibers, though this techniques also causes the edges of the object in the image to be less sharp. The low-pass spatial filter technique was implemented by several different impulse response matrices with the image. Spatial filtering is a convolution operation expressed as: $G(x, y) = F(x, y) \times H(x, y)$. G is the output image, F is the input image and H is the input response matrix. A $5 \times 5$ pyramid shaped input response matrix worked the best.

Edge crispening is a process which accentuates the edges of an image to produce an image which is subjectively more pleasing. It also enhances high spatial frequency objects or edges which would be difficult to detect ordinarily. One method of edge crispening is called unsharp masking, where a low-pass filter image is subtracted from the normal image. This is expressed as $F_M(j,k) = cF(j,k) - (1-C)F_L(j,k)$. $F_M$ is the unsharp mask image, $F_L$ is the input image, F is the low pass filter image and C is a weighting factor. This technique does a fairly good job of enhancing the U.S. Air Force Bar Target image. Another method of edge crispening is to apply discrete convolutional filtering in which the input response rate H is of high pass form.

Besides image enhancement, image restoration techniques are also available. Image restoration is an estimation process in which operations are performed on an image to generate an image which approximates the original before it was degraded by the imaging system. The Vicom (TM) image processing unit in the fiber optic inspection system has a singular value decomposition algorithm built into its library of standard routines. Using this library routine, a restored image can be generated based on a mathematical model of a degraded image.

To further automate the inspection process the video signal can be fed to the computer. A pattern recognition program can be employed to compare the digital image processor signal to a predetermined inspection criteria. The computer could reject or accept the package being inspected based on the comparation.

The embodiment of the invention in which an exclusive property or right is claimed are defined as follows:

1. A method of inspecting regions within integrated circuit packages that are visibly occluded to the naked eye, the method comprising the steps of:
   illuminating at least one occluded region of a selected integrated circuit package desired to be inspected;
   inserting a miniature fiber optic bundle into this integrated circuit package to the occluded region so illuminated;
   transmitting the optical images so obtained to a video camera;
   tranducing the optical images to a video signal; and
   displaying images obtained from the video signal on a video monitor.

2. The method of claim 1 wherein the occluded area contains solder bonds.

3. A method of inspecting regions within integrated circuit packages that are visibly occluded to the naked eye, the method comprising the steps of:
   illuminating at least one occluded region of a selected integrated circuit package desired to be inspected;
   inserting a minature fiber optic bundle into this integrated circuit package to the occluded region so illuminated;
   transmitting the optical images so obtained to a video camera for conversion of the optical images to a video signal;
   processing the video signal to enhance quality of images to be obtained therefrom; and
   displaying images obtained from the video signal as so enhanced on a video monitor.

4. The method of claim 3 wherein the occluded area contains solder bonds.

5. The method of claim 3 wherein the video image enhancement is done by contrast manipulation techniques.

6. The method of claim 3 wherein the video image enhancement is done by noise cleaning techniques.

7. The method of claim 3 wherein the video image enhancement is done by edge crispening techniques.

8. A method of inspecting regions within integrated circuit packages that are visibly occluded to the naked eye, the method comprising the steps of:
- illuminating at least one occluded region of a selected integrated circuit packaged designed to be inspected;
- inserting a miniature fiber optic bundle into this integrated circuit package to the occluded region so illuminated;
- converting the optical images so obtained to a video signal;
- processing the video signal to generate an enhanced video signal from which images can be obtained which better approximate the original optical image; and
- displaying images obtained from the enhanced video signal on a video monitor.

9. The method of claim 8 wherein the video signal is restored by a singular value decomposition algorithm routine.

10. An automated method of inspecting regions within integrated circuit packages that are visibly occluded to the naked eye, the method comprising:
- illuminating at least one occluded region of a selected integrated circuit package desired to be inspected;
- inserting under control of a computer a miniature fiber optic bundle into the integrated circuit package to the occluded region so illuminated;
- converting the optical images so obtained from the fiber optic bundle to a video signal; and
- displaying images obtained from the video signal on a video monitor 11. The method of claim 10 wherein pattern recognition is used to determine package quality by comparing the solder bond images received to a predetermined inspection criteria.

12. An image pickup apparatus which comprises:
- a light source means for providing illuminating light;
- image transmission means comprising a fiber optic bundle for sensing through a lens, fixed with respect to the fiber optic bundle, an optical image of an illuminated subject and for transmitting that image;
- image signal converting means coupled to the image transmission means for converting optical images into a video signal; and
- video signal processor means for taking the video signal and enhancing it to provide an improvement in quality of the images obtained therefrom.

* * * * *